(12) United States Patent
Jaisser et al.

(10) Patent No.: US 10,059,946 B2
(45) Date of Patent: *Aug. 28, 2018

(54) METHOD FOR TREATMENT OF HEART FAILURE

(71) Applicants: Frédéric Jaisser, Paris (FR); Nicolette Farman, Paris (FR)

(72) Inventors: Frédéric Jaisser, Paris (FR); Nicolette Farman, Paris (FR)

(73) Assignee: INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/250,007

(22) Filed: Aug. 29, 2016

(65) Prior Publication Data
US 2017/0002358 A1 Jan. 5, 2017

Related U.S. Application Data

(63) Continuation of application No. 13/991,182, filed as application No. PCT/EP2011/071779 on Dec. 5, 2011, now Pat. No. 9,533,041.

(30) Foreign Application Priority Data

Dec. 3, 2010 (EP) ..................................... 10306344

(51) Int. Cl.
| | | |
|---|---|---|
| *A61K 39/395* | (2006.01) |
| *C07K 16/32* | (2006.01) |
| *C12N 15/113* | (2010.01) |
| *A61K 31/7105* | (2006.01) |
| *A61K 31/713* | (2006.01) |
| *C12N 15/115* | (2010.01) |
| *A61K 31/7088* | (2006.01) |

(52) U.S. Cl.
CPC ...... *C12N 15/1135* (2013.01); *A61K 31/7088* (2013.01); *A61K 31/713* (2013.01); *A61K 31/7105* (2013.01); *A61K 39/3955* (2013.01); *C07K 16/32* (2013.01); *C12N 15/115* (2013.01); *C07K 2317/76* (2013.01); *C12N 15/113* (2013.01); *C12N 2310/11* (2013.01); *C12N 2310/12* (2013.01); *C12N 2310/14* (2013.01); *C12N 2310/16* (2013.01); *C12N 2320/30* (2013.01)

(58) Field of Classification Search
CPC . C07K 16/32; C07K 2317/76; A61K 39/3955
See application file for complete search history.

(56) References Cited

U.S. PATENT DOCUMENTS

2008/0095782 A1* 4/2008 Xu .................. A61K 31/44
424/139.1
2009/0274709 A1* 11/2009 Xu .................. C07K 14/47
424/172.1

FOREIGN PATENT DOCUMENTS

WO WO2009/132510 * 5/2009

* cited by examiner

*Primary Examiner* — Robert S Landsman
*Assistant Examiner* — Bruce D. Hissong
(74) *Attorney, Agent, or Firm* — Whitham & Cook, P.C.

(57) ABSTRACT

The present invention relates to an inhibitor of NGAL gene expression or a NGAL antagonist for use in the prevention or the treatment of heart failure.

1 Claim, 7 Drawing Sheets

METHOD FOR TREATMENT OF HEART FAILURE

FIELD OF THE INVENTION

Figure 1:
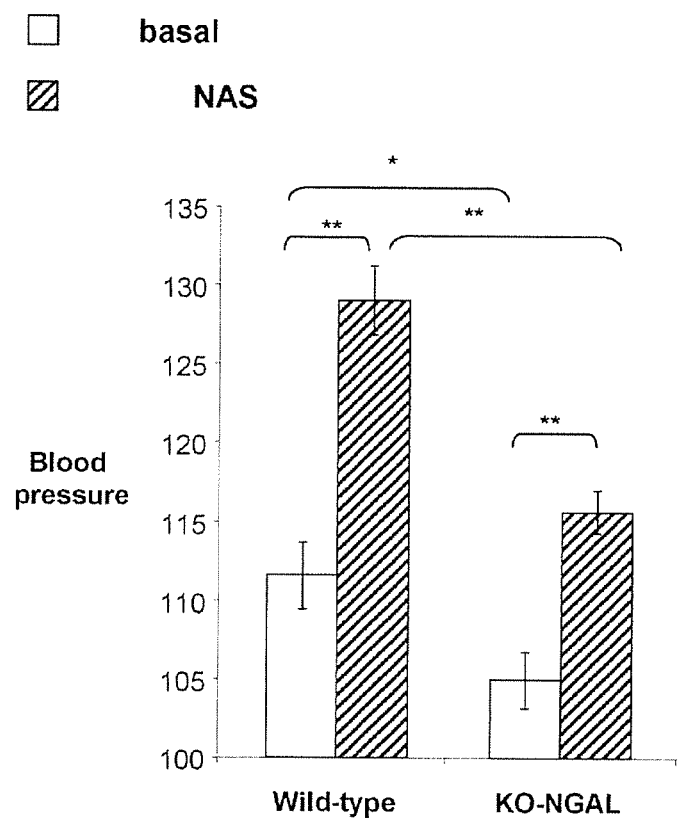

The present invention relates to an inhibitor of NGAL gene expression or a NGAL antagonist for use in the prevention or the treatment of heart failure.

BACKGROUND OF THE INVENTION

Heart failure occurs when the heart is damaged from diseases such as high blood pressure, a heart attack, poor blood supply to the heart, a defective heart valve, atherosclerosis, rheumatic fever, heart muscle disease and so on. The failing heart becomes inefficient, resulting in fluid retention and shortness of breath, fatigue and exercise intolerance. Heart failure is defined by the symptom complex of dyspnea, fatigue and depressed left ventricular systolic function (ejection fraction<35-40%), and is the ultimate endpoint of all forms of serious heart disease. Despite considerable advances in treatment, heart failure remains associated with high morbidity and mortality.

Heart failure has many causes and pathophysiological origins. For example, aldosterone could have a role in endothelial dysfunction in chronic heart failure and accordingly, mineralocorticoid receptor (MR) is an important drug target particularly for the treatment of heart failure. For example, the aldosterone antagonist spironolactone (also known as ALDACTONE®, PFIZER) is used commonly in the treatment of congestive heart failure. Actually, spironolactone has been shown to be pharmacologically effective and well tolerated, to reduce the overall risks of death, death due to progressive heart failure, and sudden death from cardiac causes, as well as the risk of hospitalization for cardiac causes. Likewise, eplerenone exemplifies another blocker of aldosterone binding at the mineralocorticoid receptor. The therapeutic benefits of eplerenone for the treatment of heart failure have been recently demonstrated in clinical trials.

The neurophil gelatinase-associated lipocalin (NGAL) is a member of the lipocalin family which has been previously identified as a molecular target of aldosterone through the activation of the mineralocorticoid receptor, a ligand-activated transcription factor. NGAL is able to form a complex with the metalloprotease 9 (MMP9) and increases MMP9 activity by increasing its stability. It was previously showed that tissue expression of NGAL as well as plasma level of NGAL is increased in pathophysiological situations when aldosterone and/or MR is activated in the cardiovascular system and in the metabolic syndrom, both in experimental models and in human patients. Moreover a correlation between the plasma NGAL-MMP9 and plasma aldosterone level has been identified.

Lipocalins are a widely distributed group of proteins which have the ability to bind and transport small hydrophobic molecules and could therefore represent a potential therapeutic target. However, the involvement of NGAL in the pathophysiological effects of aldosterone and MR activation in the heart has not yet been investigated.

SUMMARY OF THE INVENTION

The present invention relates to an inhibitor of NGAL gene expression or a NGAL antagonist for use in the prevention or the treatment of heart failure.

DETAILED DESCRIPTION OF THE INVENTION

The invention provides methods and compositions (e.g. pharmaceutical compositions) for use in the prevention or treatment of heart failure in a patient.

More particularly, the present invention relates to an inhibitor of NGAL gene expression or a NGAL antagonist for use in the treatment of heart failure.

As used herein, the terms "Lipocalin 2" (Lcn2) or "NGAL" have their general meaning in the art and refer to the Neutrophil Gelatinase-Associated Lipocalin as described in Schmidt-Ott K M et al. (2007). NGAL can be from any source, but typically is a mammalian (e.g., human and non-human primate) NGAL, particularly a human NGAL. The term "NGAL gene" refers to any nucleotide sequence encoding the NGAL mRNA and protein, such as a genomic DNA sequence and any naturally occurring NGAL and variants and modified forms thereof. It can also encompass artificial sequences such as cDNA encoding the NGAL mRNA and protein. An exemplary human native NGAL nucleotide sequence is provided in GenBank database under accession number NM_005564. The term "NGAL mRNA" has its general meaning in the art and refers to the messenger RNA which is synthesized upon expression of the NGAL gene. The term "NGAL protein" refers to the amino acid sequence resulting from the expression of the NGAL gene, and any naturally occurring NGAL and variants and modified forms thereof. An exemplary human native NGAL amino acid sequence is provided in GenPept database under accession number NP_005555. NGAL is a glycoprotein and was originally identified as a neutrophil specific granule component and a member of the lipocalin family of proteins. The protein was shown to exist both as a 25-kDa monomer and a 45-kDa disulfide-linked homodimer, and it may also be covalently complexed with neutrophil gelatinase (also known as matrix metalloproteinase 9, MMP-9) via an intermolecular disulphide bridge as a 135-kDa heterodimeric form.

As used herein, the term "patient" denotes a mammal, such as a rodent, a feline, a canine, and a primate. Preferably, a patient according to the invention is a human.

The term "heart failure" (HF) as used herein embraces congestive heart failure and/or chronic heart failure. Functional classification of heart failure is generally done by the New York Heart Association Functional Classification (Criteria Committee, New York Heart Association. Diseases of the heart and blood vessels. Nomenclature and criteria for diagnosis, 6th ed. Boston: Little, Brown and co, 1964;114). This classification stages the severity of heart failure into 4 classes (I-IV). The classes (I-IV) are:

Class I: no limitation is experienced in any activities; there are no symptoms from ordinary activities.

Class II: slight, mild limitation of activity; the patient is comfortable at rest or with mild exertion.

Class III: marked limitation of any activity; the patient is comfortable only at rest.

Class IV: any physical activity brings on discomfort and symptoms occur at rest.

In one embodiment, the present invention relates to an inhibitor of NGAL gene expression or a NGAL antagonist for use in the treatment or prevention of heart failure is associated with the activation of the mineralocorticoid receptor.

The present invention also relates to an inhibitor of NGAL gene expression or an NGAL antagonist for use in the prevention of heart failure in a patient who is susceptible to develop heart failure. For example, the patient may be diagnosed with a genetically linked cardiovascular disease, hypertension (high blood pressure), pulmonary hypertension, aortic and mitral valve disease (e.g. stenosis), aortic coarctation, coronary disorders, chronic arrhythmias (e.g. atrial fibrillation), cardiomyopathy of any cause, coronaropathy, valvulopathy or cardiac fibrosis. In another particular embodiment, the patient may be at risk for heart failure because of diabetes, obesity, aging, smoking, dyslipidemia, intoxication or a genetic disease.

An "inhibitor of gene expression" refers to a natural or synthetic compound that has a biological effect to inhibit or significantly reduce the expression of a gene. Thus, an "inhibitor of NGAL gene expression" refers to a natural or synthetic compound that has a biological effect to inhibit or significantly reduce the expression of the gene encoding for NGAL. In a preferred embodiment, the inhibitor of NGAL gene expression according to the invention specifically inhibits the expression of NGAL in the heart (i.e. cardiac cells).

Inhibitors of NGAL gene expression for use in the present invention may be based on anti-sense oligonucleotide constructs. Anti-sense oligonucleotides, including anti-sense RNA molecules and anti-sense DNA molecules, would act to directly block the translation of NGAL mRNA by binding thereto and thus preventing protein translation or increasing mRNA degradation, thus decreasing the level of NGAL, and thus activity, in a cell. For example, antisense oligonucleotides of at least about 15 bases and complementary to unique regions of the mRNA transcript sequence encoding NGAL can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) may also function as inhibitors of NGAL gene expression for use in the present invention. NGAL gene expression can be reduced by contacting a subject or cell with a small double stranded RNA (dsRNA), or a vector or construct causing the production of a small double stranded RNA, such that NGAL gene expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes may also function as inhibitors of NGAL gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of NGAL mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of NGAL gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing NGAL. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In a particular embodiment, the antisense oligonucleotide, siRNA, shRNA or ribozyme nucleic acid sequence is under the control of a heterologous regulatory region, e.g., a heterologous promoter.

In another aspect, the present invention relates to an NGAL antagonist for use in the prevention or the treatment of heart failure.

The term "NGAL antagonist" refers to a compound, natural or not, which has the capability to inhibit (partly or totally) the biological activity of the NGAL protein. The scope of the present invention includes all those NGAL antagonists now known and those NGAL antagonists to be discovered in the future. This term includes anti-NGAL antibody whereby the biological activity of NGAL is inhibited. The term "anti-NGAL antibody" refers to an antibody or a fragment thereof which recognizes NGAL. In a preferred embodiment, the NGAL antagonist specifically inhibits the biological activity in the heart (i.e. cardiac cells). Typically, the NGAL antagonist according to the invention may target the ligand binding site as described in Grzyb J. et al. (Journal of Plant Physiology 163 (2006) 895-915) and Flower DR. et al. (Biochimica et Biophysica Acta 1482 (2000) 9-24).

In one embodiment the NGAL antagonist may consist in an antibody (the term including antibody fragment) that can block NGAL activity.

Antibodies directed against the NGAL can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against NGAL can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see, e.g., U.S. Pat. No. 4,946,778) can be adapted to produce anti-NGAL single chain antibodies. NGAL antagonists useful in practicing the present invention also include anti-NGAL antibody fragments including but not limited to F(ab')$_2$ fragments, which can be generated by pepsin digestion of an intact antibody molecule, and Fab fragments, which can be generated by reducing the disulfide bridges of the F(ab')$_2$ fragments. Alternatively, Fab and/or scFv expression libraries can be constructed to allow rapid identification of fragments having the desired specificity to NGAL Humanized anti-NGAL antibodies and antibody fragments therefrom can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

Then after raising antibodies directed against the NGAL as above described, the skilled man in the art can easily select those blocking NGAL activity.

In another embodiment the NGAL antagonist is an aptamer directed against NGAL. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996). Then after raising aptamers directed against the NGAL as above described, the skilled man in the art can easily select those blocking NGAL activity.

In still another embodiment, the NGAL antagonist may be a low molecular weight antagonist, e. g. a small organic molecule. The term "small organic molecule" refers to a molecule of a size comparable to those organic molecules generally used in pharmaceuticals. The term excludes biological macromolecules (e. g., proteins, nucleic acids, etc.). Preferred small organic molecules range in size up to about 5000 Da, more preferably up to 2000 Da, and most preferably up to about 1000 Da.

Typically, the small organic molecule may target the ligand binding site as described in Grzyb J. et al. (Journal of Plant Physiology 163 (2006) 895-915) and Flower DR. et al. (Biochimica et Biophysica Acta 1482 (2000) 9-24) and thus impends the binding between NGAL and its ligands.

The inhibitor NGAL gene expression or the NGAL antagonist may be administered in the form of a pharmaceutical composition. Preferably, said inhibitor or antagonist is administered in a therapeutically effective amount.

By a "therapeutically effective amount" is meant a sufficient amount of the NGAL antagonist or inhibitor to treat and/or to prevent heart failure at a reasonable benefit/risk ratio applicable to any medical treatment.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The inhibitor of NGAL gene expression or the NGAL antagonist for use in the prevention or the treatment of heart failure as defined above may be combined with pharmaceutically acceptable excipients, and optionally sustained-release matrices, such as biodegradable polymers, to form therapeutic compositions.

In the pharmaceutical compositions of the present invention, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The inhibitor of NGAL gene expression or the NGAL antagonist of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils.

The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The inhibitor of NGAL gene expression or the NGAL antagonist of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

The invention will be further illustrated by the following figures and examples. However, these examples and figures should not be interpreted in any way as limiting the scope of the present invention.

FIGURES

FIG. 1. Effect on blood pressure of aldo-salt in WT and KO-NGAL mice.

Figure 2:
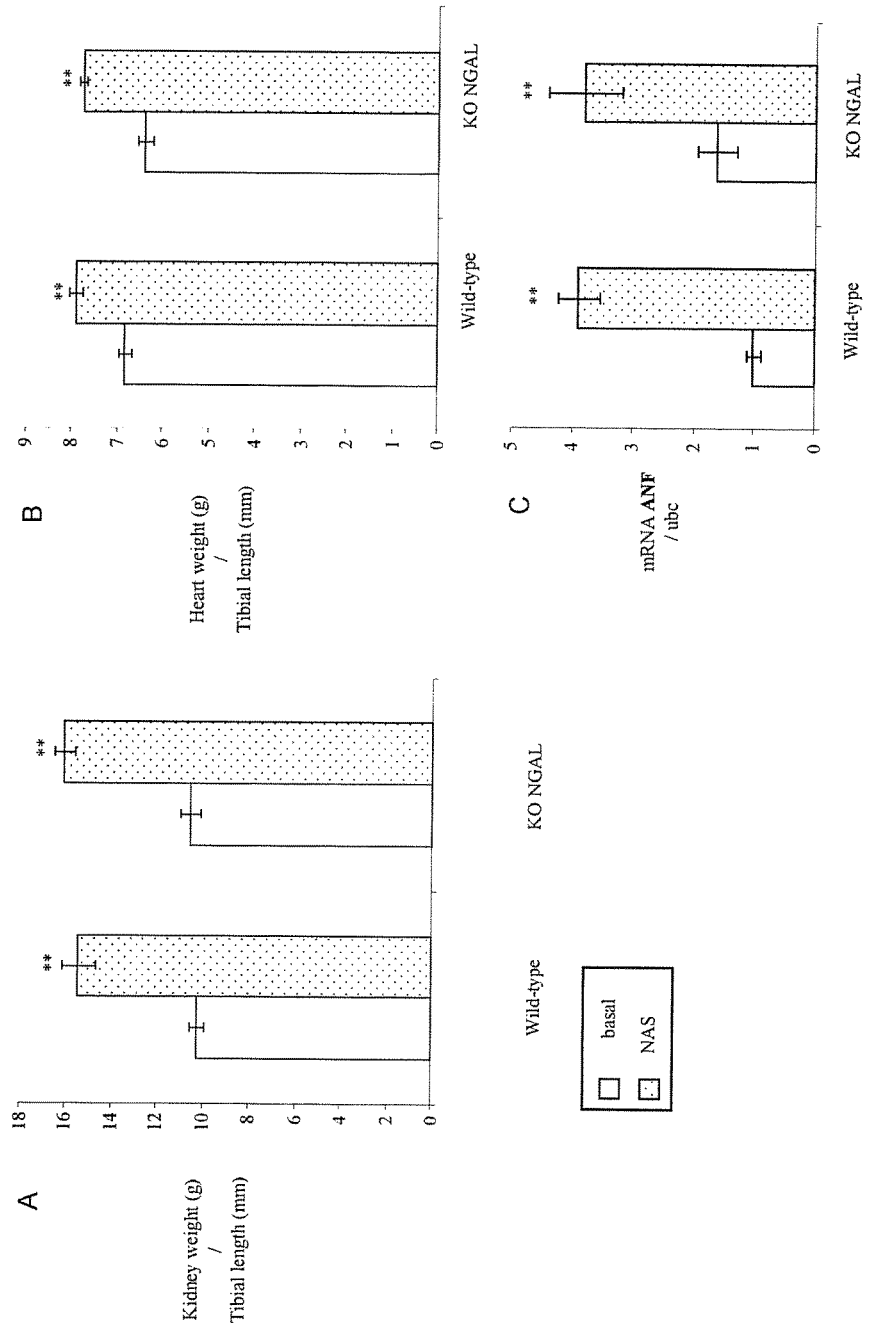

FIG. 2. Effect of aldo-salt on heart weight/tibial length and kidney/tibial length ratios in WT and KO-NGAL mice.

Figure 3:
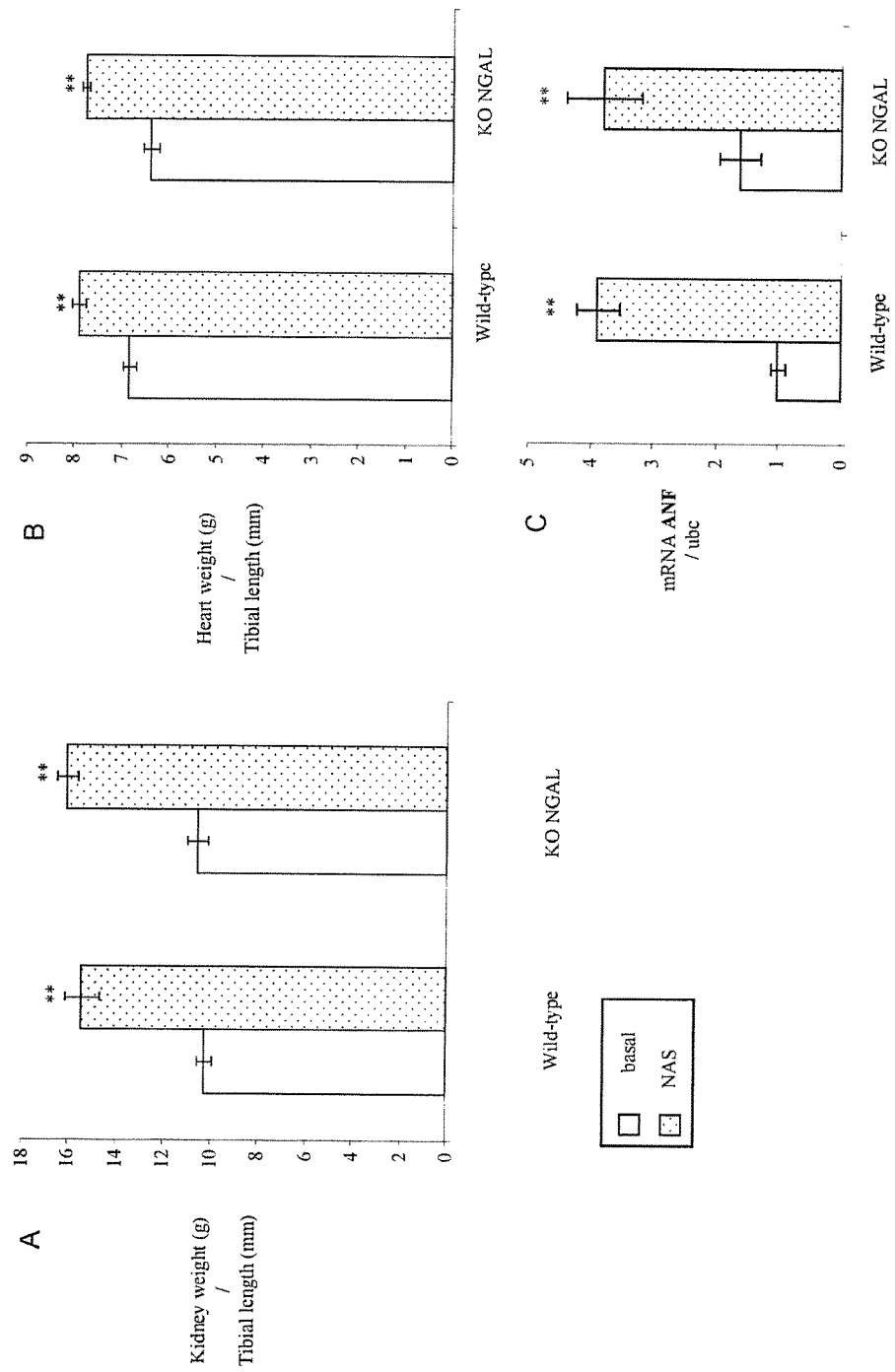

FIG. 3. Effect of aldo-salt on extracellular marix remodeling in WT and KO-NGAL mice FIG. 4. Effect of aldo-salt on MMP expression/activity in WT and KO-NGAL mice FIG. 5. Effect of aldo-salt on inflammation markers in WT and KO-NGAL mice FIG. 6. Effect of aldo-salt on MCP1 and macrophage markers in WT and KO-NGAL mice.

Figure 7:
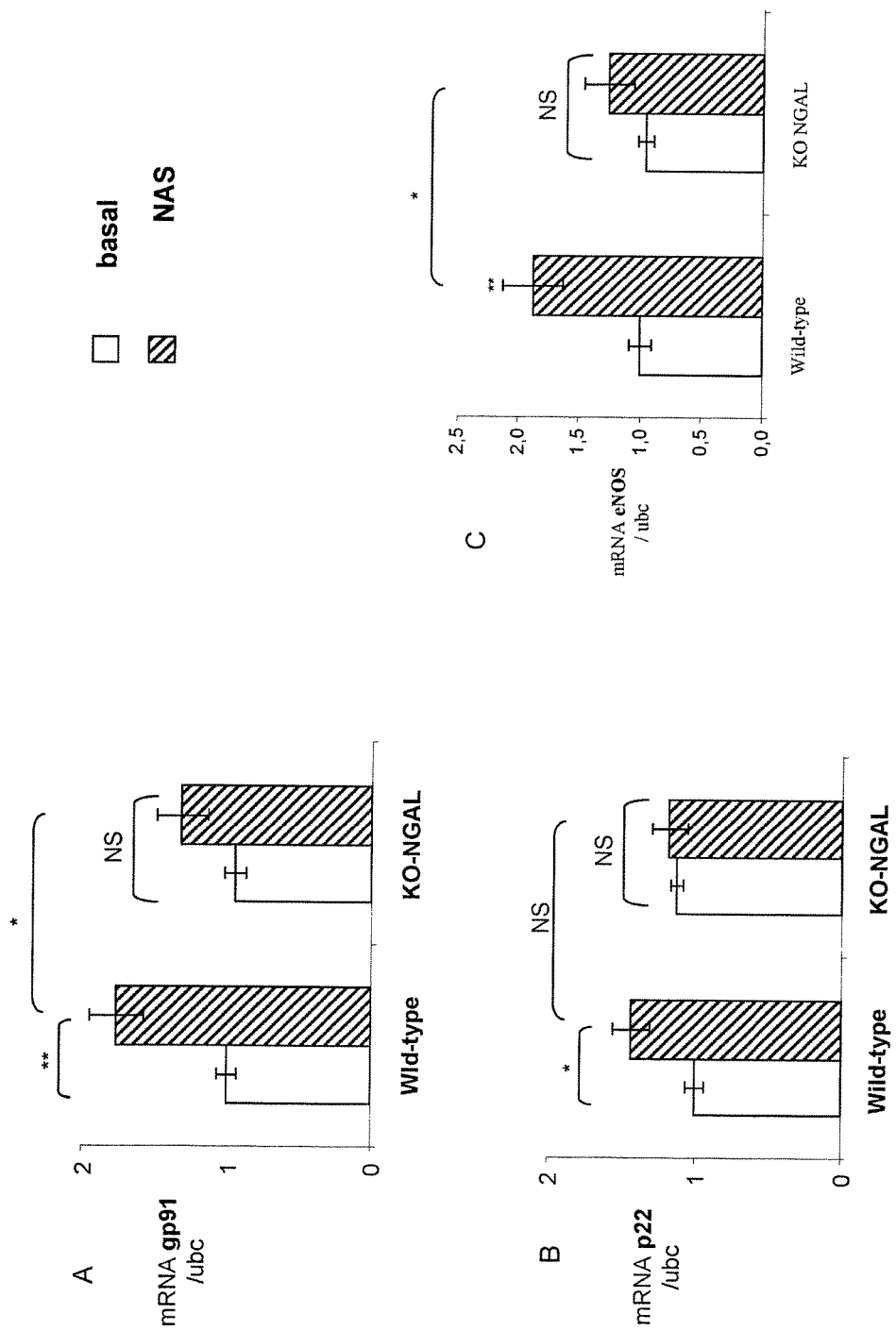

FIG. 7. Effect of aldo-salt on oxidative stress markers in WT and KO-NGAL mice

EXAMPLE

Summary: In order to identify if NGAL is a biotarget of aldosterone/MR involved in the pathophysiological consequences of aldosterone/MR activation, in addition to be a MR-regulated gene and a putative biomarker of MR activation, experiments were designed using a mouse model with genetic gene inactivation of NGAL. NGAL KO mice and their wild-type controls were infused with aldosterone and salt, a classical experimental protocol aimed to activate MR in vivo. We next analyzed molecular, histological and functional parameters in the various experimental groups. The data indicated that the NGAL was essential for the induction of various signaling pathways upon MR activation in the heart, indicating that interfering with NGAL expression/activity may be of therapeutical interest in pathophysiological situations with MR activation.

Methods: 3 months old uni-nephrectomized C57 wild-type mice and KO-NGAL mice were infused subcutaneously with aldosterone (60 ug/Kg/day) in AZLET minipumps, in addition to 1% NaCl in the drinking water for 4 weeks. Heart and kidney weights were analyzed at sacrifice, and mRNA was prepared from heart tissues. Expression of various genes was analyzed by Q-PCR using appropriate oligos. Ubiquituin C (ubc) is used as an endogenous reference gene. MMP9 activity was analyzed on cardiac protein extracts using Invitrogen Novex gels Zymogra.

Results: Blood pressure was slightly but significantly lower in KO-NGAL mice as compared to wild-type in the basal conditions. Blood pressure increase induced by Aldo-salt (NAS) is slightly lower in KO-NGAL than in wild-type mice (FIG. 1).

Aldo-salt (NAS) induces a similar increase in kidney (panel A) and cardiac weight (panel B) (as estimated by organ weight on tibial length). Expression of the atrial natriuretic factor (ANF, panel C) is similar between KO-NGAL and WT mice, indicating similar cardiac response to blood pressure increase and wall stretch (FIG. 2).

The increase in Collagen 1 (Col I) (panel A), periostin (panel B) and fibronectin 1 (panel D) by aldo-salt (NAS) observed in wild-type mice is blunted in KO-NGAL mice while expression of Collagen 3 (Col3) (panel C) is not affected by aldo-salt (NAS) neither in wild-type or KO-NGAL mice (FIG. 3).

Figure 4:
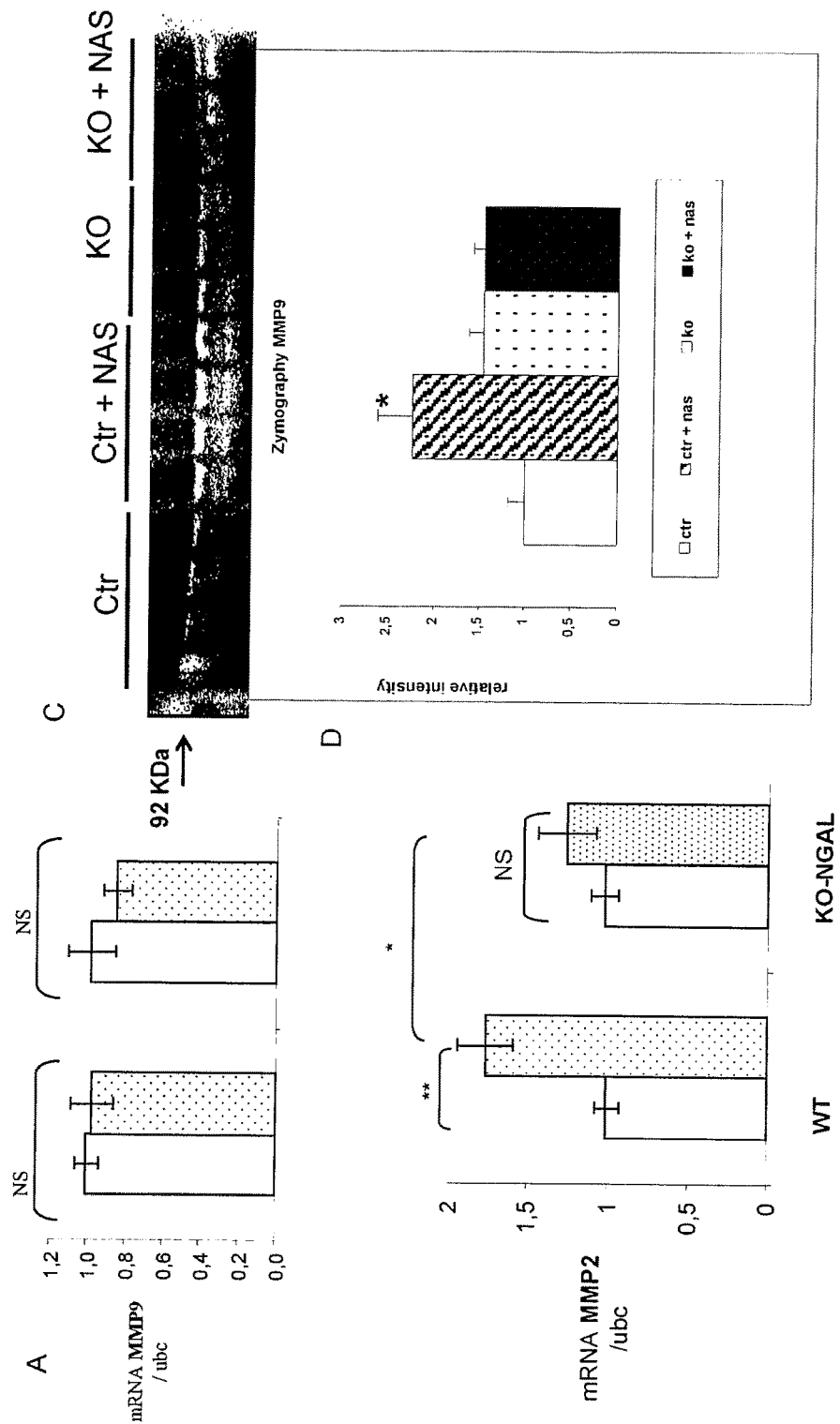

Expression level of MMP9 (panel A) is not affected by aldo salt (NAS), neither in control or KO-NGAL mice, at difference to MMP2 (panel B) which expression is induced by aldo-salt (NAS) in wild-type mice but not in KO-NGAL mice (FIG. 4). In contrast MMP9 activity (panel C, zymogram; panel D quantification of zymogram) is induced by aldo-salt (NAS) in wild-type mice. This induction is blunted in KO-NGAL mice.

Figure 5:
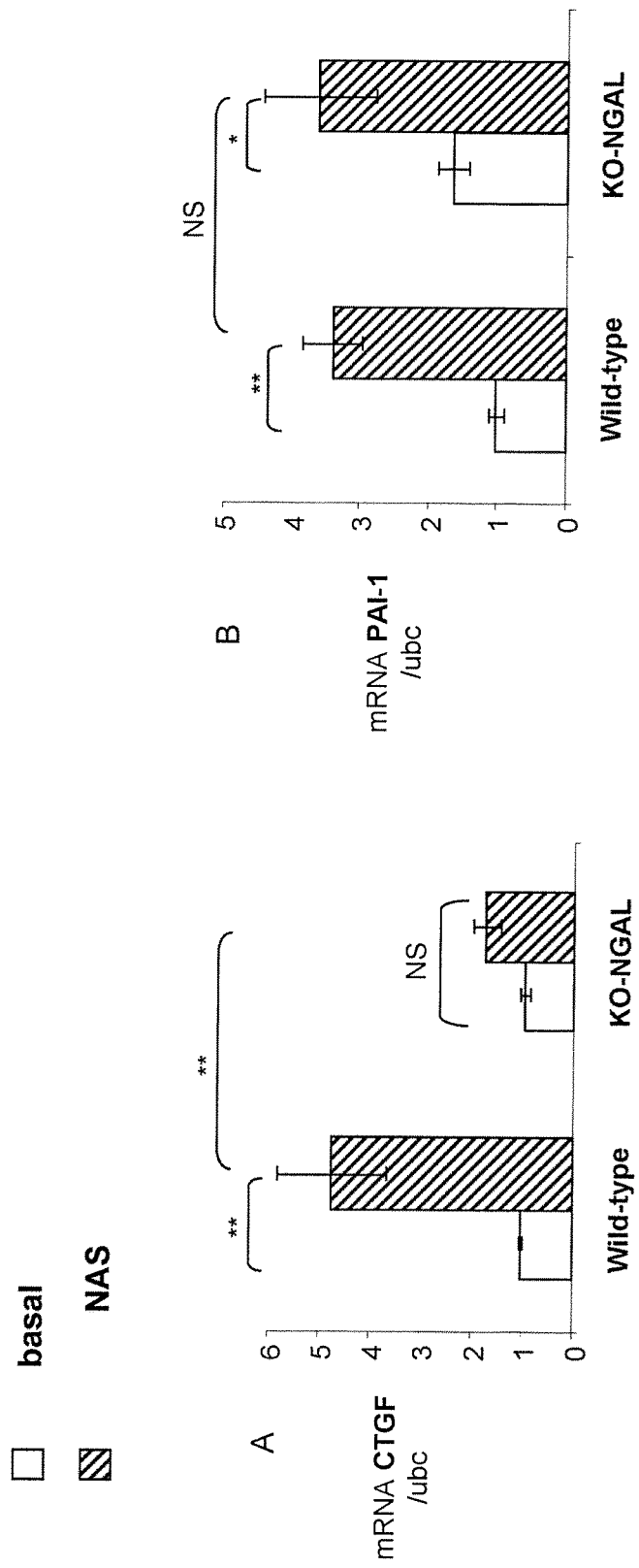

The increase in the expression of Connective Tissue Growth Factor (CTGF, panel A) by aldo-salt (NAS) is blunted in KO-NGAL mice expression while expression of plasminogen activator inhibitor (PAI 1, panel B) is similarly increased by aldo-salt (NAS) in control or KO-NGAL mice (FIG. 5).

Figure 6:
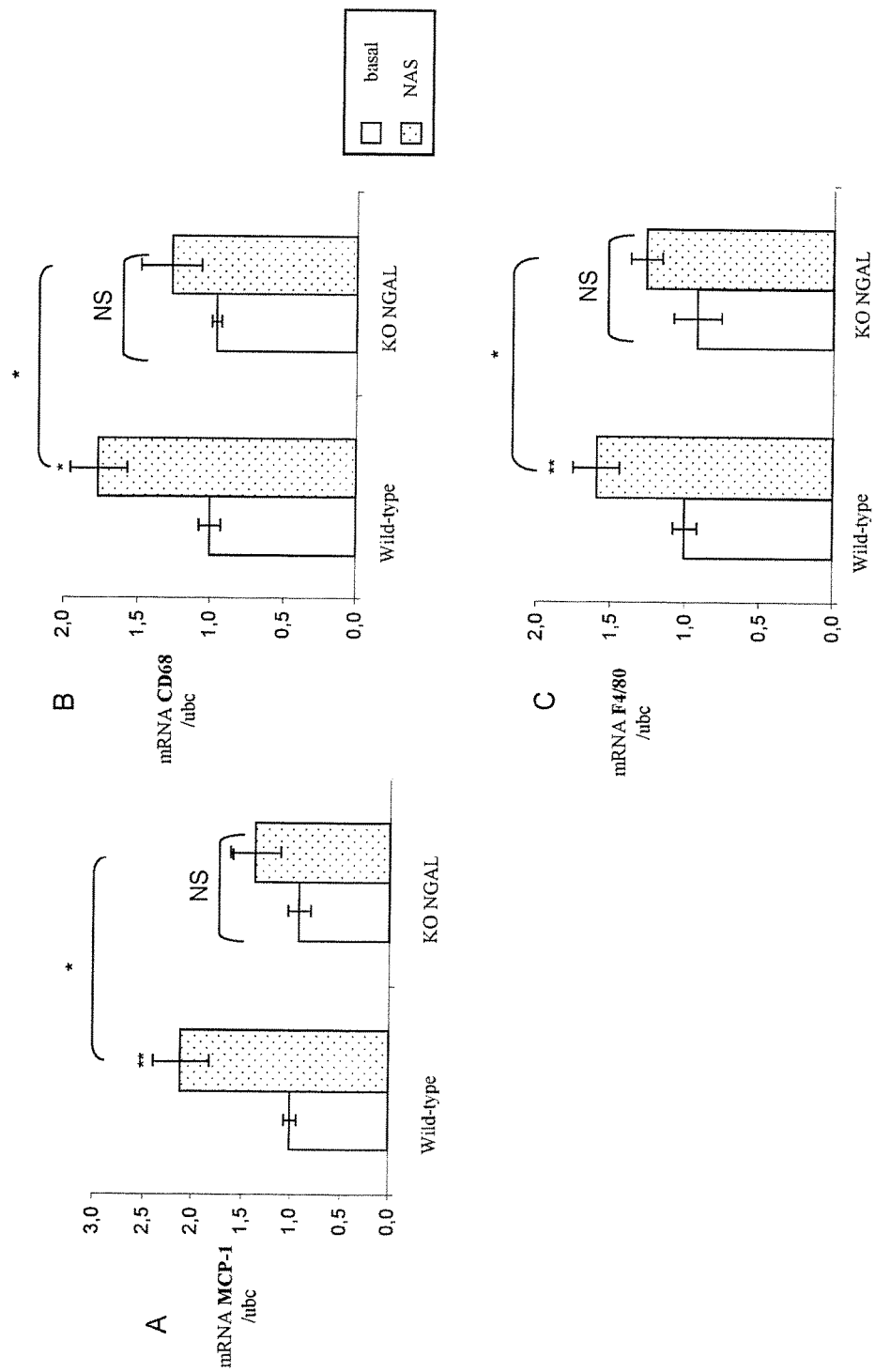

The increase in Monocyte chemoattractant protein-1 (MCP 1, panel A) and the macrophage markers CD68 (panel B) and F4/F80 (panel C) by aldo-salt (NAS) observed in wild-type mice is blunted in KO-NGAL mice (FIG. 6).

The increase of genes involved in oxidative stress such as the p91 (panel A) and p22 (panel B) subunits of the NADPH oxidase and the endothelial nitric oxide synthase (eNOS) (panel C) by aldo-salt (NAS) observed in wild-type mice is blunted in KO-NGAL mice (FIG. 7).

Conclusion: These data indicate that NGAL is not only a gene regulated by mineralocorticoid receptor activation but also a biotarget involved in the pathophysiological effects of aldosterone and MR activation in the heart. Genetic NGAL gene inactivation (KO-NGAL mice) prevents the activation of several pathways induced by MR activation in the heart such as 1) extracellular matrix remodeling process (coil, fibronectin, CTGF, MMP 9 activity); 2) inflammation (macrophages recruitment through MCP1 expression), 3) oxidative stress (gp91 and p22 NADPH oxidase subunits, eNOS). A mild but significant effect is observed on blood pressure, already present in basal conditions (suggesting that NGAL may also be involved in blood pressure regulation). However NGAL inactivation does not prevent renal and cardiac hypertrophy induced by aldo-salt, probably related to the increased blood pressure induced by aldo-salt due to its renal effects.

NGAL could therefore be proposed as a drugable target, in the context of MR activation in cardiovascular disease.

REFERENCES

Throughout this application, various references describe the state of the art to which this invention pertains. The disclosures of these references are hereby incorporated by reference into the present disclosure.

The invention claimed is:

1. A method of treating congestive heart failure or chronic heart failure in a patient in need thereof, wherein said congestive heart failure and said chronic heart failure are heart failures induced by mineralcorticoid receptor (MR) activation, comprising
   administering to the patient a therapeutically effective amount of a neutrophil gelatinase-associated lipocalin (NGAL) antagonist, wherein said NGAL antagonist is an antibody which specifically inhibits the biological activity of NGAL in cardiac cells to treat said congestive heart failure or chronic heart failure induced by MR activation and wherein said antibody is in the form of a pharmaceutical composition.

* * * * *